United States Patent [19]

Snow

[11] Patent Number: 5,028,232
[45] Date of Patent: Jul. 2, 1991

[54] APPARATUS AND METHOD FOR CALIBRATING PHYSIOLOGIC DENTAL OCCLUSION AND DETERMINING OPTIMAL INDIVIDUAL ORTHODONTIC APPLIANCE PRESCRIPTION

[76] Inventor: Michael D. Snow, 22 Prince Street, Mornington 3931, Victoria, Australia, 059 751392

[21] Appl. No.: 346,901

[22] Filed: May 3, 1989

[51] Int. Cl.⁵ .................... A61C 3/00; A61C 19/04
[52] U.S. Cl. ........................... 433/24; 433/72; 433/68
[58] Field of Search ............... 433/68, 69, 71, 45, 433/46, 56, 53, 24, 2, 196, 72, 73

[56] References Cited

U.S. PATENT DOCUMENTS

| | | |
|---|---|---|
| 1,188,416 | 6/1916 | Dalbey . |
| 1,411,505 | 4/1922 | Northwood ............... 433/45 |
| 1,518,075 | 12/1924 | Kesling ................. 433/56 X |
| 1,589,973 | 6/1926 | Landa . |
| 1,831,390 | 11/1931 | Lindelov . |
| 1,910,740 | 5/1933 | Barsha .................. 433/71 X |
| 2,040,835 | 5/1936 | Cubbage .................. 33/174 |
| 2,475,706 | 7/1949 | Jamieson ................. 33/174 |
| 2,491,136 | 12/1949 | Salzmann ................. 33/174 |
| 2,510,152 | 6/1950 | Stoll ....................... 32/32 |
| 2,528,153 | 10/1950 | Legge ....................... 32/19 |
| 2,545,249 | 3/1951 | Ackerman .................. 32/32 |
| 2,701,915 | 2/1955 | Page ........................ 433/69 |
| 2,724,899 | 11/1955 | Stoll ........................ 33/174 |
| 3,023,502 | 3/1962 | Vaughan ..................... 32/40 |
| 3,137,941 | 6/1964 | Andrews ...................... 32/14 |
| 3,321,832 | 5/1967 | Weisberg ................. 433/56 X |
| 3,335,496 | 8/1967 | Andrews et al. ............... 32/14 |
| 3,439,421 | 4/1969 | Perkowski ................... 32/14 |
| 3,474,536 | 10/1969 | Andrews .................... 32/14 |
| 3,477,128 | 11/1969 | Andrews .................... 32/14 |
| 3,521,354 | 7/1970 | Stern et al. ................. 32/11 |
| 3,521,355 | 7/1970 | Pearlman .................... 32/14 |
| 3,657,817 | 4/1972 | Kesling .................... 32/14 A |
| 3,660,900 | 5/1972 | Andrews .................. 32/14 A |
| 3,745,665 | 7/1973 | Shilliday ................. 33/174 D |
| 3,881,252 | 5/1975 | Andrews ................. 32/14 A |
| 3,900,953 | 8/1975 | Posen ....................... 32/40 R |
| 3,918,159 | 11/1975 | Andrews ................. 32/14 D |
| 3,922,786 | 12/1975 | Lavin ........................ 32/11 |
| 3,930,311 | 1/1976 | Andrews ................. 32/14 A |
| 3,949,477 | 4/1976 | Cohen et al. ............. 32/14 A |
| 3,949,478 | 4/1976 | Schinhammer ........... 32/14 A |
| 3,983,628 | 10/1976 | Acevedo .................. 32/14 E |
| 4,096,637 | 6/1978 | Stade .................... 33/174 D |
| 4,097,993 | 7/1978 | Andrews ................. 32/14 A |
| 4,182,312 | 1/1980 | Mushabac ................... 433/68 |
| 4,183,141 | 1/1980 | Dellinger et al. ............. 433/24 |
| 4,245,986 | 1/1981 | Andrews ..................... 433/5 |
| 4,360,341 | 11/1982 | Dellinger ................... 433/24 |
| 4,368,040 | 1/1983 | Weissman ............... 433/45 X |
| 4,508,506 | 4/1985 | Jackson ..................... 433/74 |
| 4,526,540 | 7/1985 | Dellinger .................. 433/24 |
| 4,543,062 | 9/1985 | Lee .......................... 433/71 |
| 4,616,998 | 10/1986 | Wong ....................... 433/73 |
| 4,668,192 | 5/1987 | Lavin ...................... 433/205 |
| 4,722,686 | 2/1988 | Salib ....................... 433/72 |
| 4,812,118 | 3/1989 | Creekmore ............. 433/53 X |

FOREIGN PATENT DOCUMENTS

| | | | |
|---|---|---|---|
| 1291854 | 4/1969 | Fed. Rep. of Germany | 433/56 |
| 2805889 | 8/1979 | Fed. Rep. of Germany | 433/69 |

Primary Examiner—Robert P. Swiatek
Assistant Examiner—Nicholas D. Lucchesi
Attorney, Agent, or Firm—Richard E. Jenkins

[57] ABSTRACT

A dental system for determining optimal orthodontic appliance prescription prior to initiation and implementation of orthodontic treatment. The system provides for measuring the pre-treatment anatomically occurring tooth positions of plaster replicas of the teeth, repositioning of such teeth to their ideal post-orthodontic treatment location in the dental occlusion, and measuring the post-treatment tooth position in order to provide for a correctly individualized orthodontic appliance prescription.

13 Claims, 11 Drawing Sheets

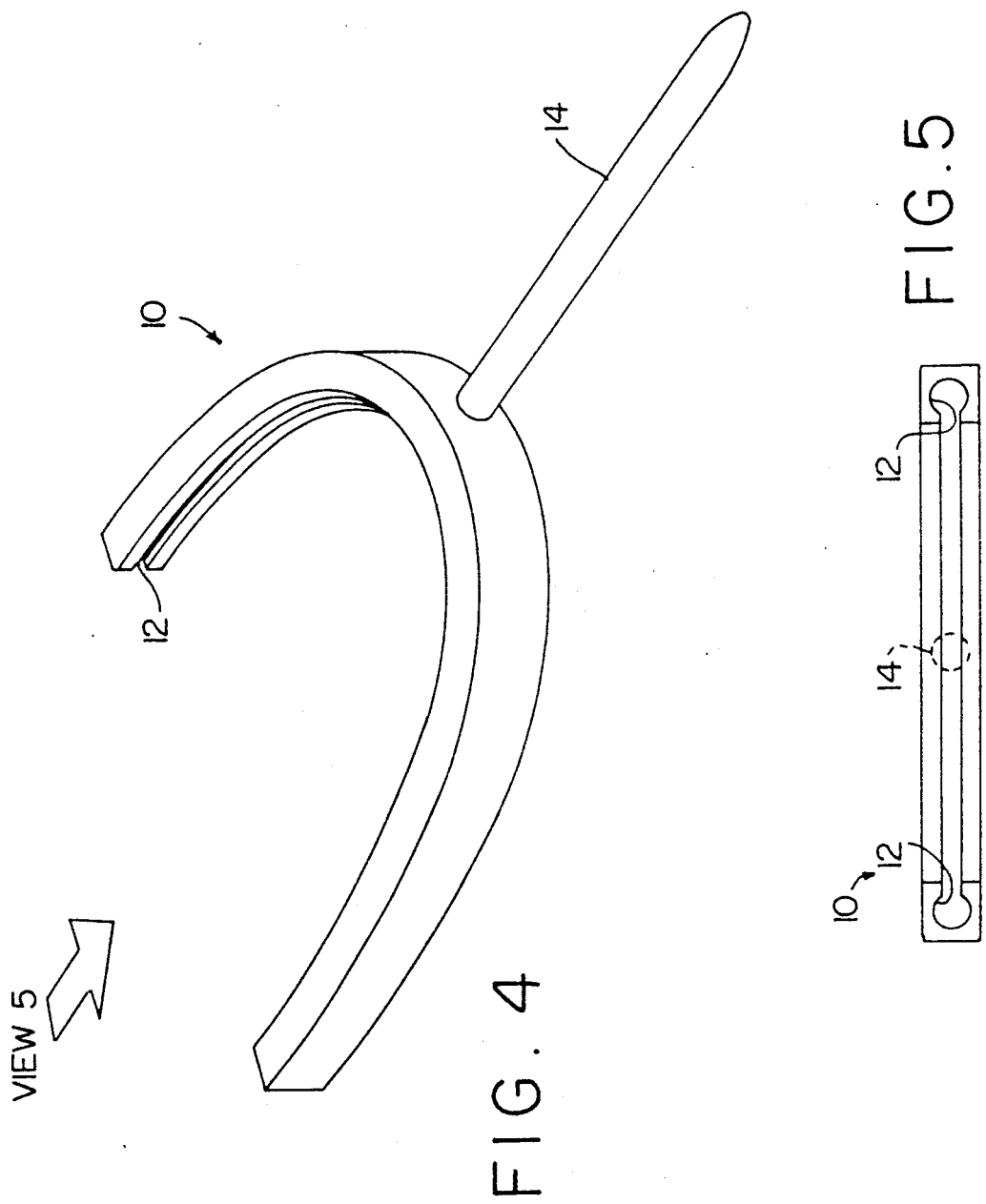

APPARATUS AND METHOD FOR CALIBRATING PHYSIOLOGIC DENTAL OCCLUSION AND DETERMINING OPTIMAL INDIVIDUAL ORTHODONTIC APPLIANCE PRESCRIPTION

TECHNICAL FIELD

The present invention relates to a dental (orthodontic) apparatus and method which is adapted to be used in conjunction with a standard dental anatomic articulator (jaw replicating device) in order to determine the optimal orthodontic tooth braces appliance prescription in order to calibrate each tooth position to anatomic and physiologic norms for an individual patient.

BACKGROUND ART

As is known by those skilled in the orthodontic art, existing orthodontic appliances ("tooth braces") purport to provide holistic prescriptions which can match all variations of individual dental occlusions to a particular population and anatomic mean. An appliance manufacturer's recommended single and non-customized orthodontic prescription appliance (tooth braces) may presently form the entire inventory of an orthodontist's office. For primarily these reasons, dental braces (orthodontic) appliance systems may have been applied by dental clinicians without the necessary absolute regard to variation in dental occlusal morphology and jaw dynamics, for and of individual patients in the population.

As is known to dental anatomists and orthodontists, each individual patient has anatomically individual characteristics with respect to dental tooth form and inherent dental occlusion that identify the individual as distinct from all others, however similar these may superficially appear. Each individual patient has an absolute, solitary dental occlusal signature that is unique to that patient. Therefore, the present practice of application of a "standardized" or "normalized" prescription for tooth positioning in dental appliance therapy in orthodontics, does not satisfy the entire demands of the individual dental prescription in a direct manner and moreover, this practice tenet relies heavily on the assumption that each individual patient will follow the central tendency of the patient population.

Therefore with all things equal, it may be appreciated that fixed orthodontic tooth attachments or tooth braces manufactured to a mean derived appliance prescription will satisfy dental occlusal requirements in any individual treatment case in the dental clinic only with subsequent individualized modifications. This contrasts to this aforesaid popularized and manufactured "blanket" orthodontic appliance approach in orthodontic mechanotherapy. The correct approach to orthodontic appliance implementation relies on the clinician to judge shortfalls during the treatment process, but most desirably, allows planned and sequenced steps prior to actual treatment implementation. The shortcoming of the present approach in orthodontic prescription is that the prescription of the absolutely correct appliance for an individual patient during the diagnostic and prognostic stage of patient care has seemingly become irrelevant, rather than absolutely necessary, to avoid any replication of treatment stages and this approach produces unnecessary "appliance induced" steps which could be potentially biologically harmful, during the long orthodontic treatment period (18-24 months) with tooth braces.

In order to overcome the deficiencies of the present state of the art in orthodontic treatment, applicant has invented a novel apparatus and method that provides for accurate and valid assessment of tooth positions and dental occlusion, so that projected optimal orthodontic appliance prescription for a particular individual patient is obtained prior to initiation of the treatment process. Calibration of tooth positions from a mechanical appraisal of physiologic individual characteristics allows provision for the optimal orthodontic appliance or tooth braces prescription prior to initiation of any orthodontic treatment. The invention minimizes incipient modification of the orthodontic appliance components during the lengthy orthodontic treatment period Thus, the present invention fulfills all of the necessary individual requirements in prescribing individual orthodontic appliances presently lacking in available appliance systems, which are designed for only an "average patient" or which are applied ad libitum to the population using the so called "anatomic mean".

DISCLOSURE OF THE INVENTION

In accordance with the present invention, applicant provides an orthodontic apparatus and method for determining optimal orthodontic appliance prescription for an individual patient through the calibration of tooth positions for an individual patient. The system allows for determining the optimal orthodontic appliance or tooth brace prescription for an individual patient by providing, firstly, for the calibration of pre-treatment tooth positions using routine dental plaster study models in a conventional dental articulator and, secondly, by providing a means to set all teeth in the plaster models in the dental articulator to the ideal and philosophically preferred dental occlusion post-treatment location prior to the implementation of orthodontic treatment with tooth braces. The pre-treatment calibration of individual tooth positions as well as the three-dimensional replication of the projected post-treatment ideal tooth position allows the clinician to best determine why, where and how far selected teeth need to be moved in an individual patient matched to individual physiology and physiognomy, and where malalignment of teeth (dental malocclusion) is present.

Applicant believes that there is no existing system which allows for these necessary steps in clinical orthodontics in order to prescribe tooth braces and which are the optimal prescription for the individual patient. Thus, an orthodontic system has been discovered which allows for both pre-treatment and post-treatment measurements of the teeth of an individual patient and most importantly, allows a rational and best orthodontic appliance prescription for any individual patient since this is desirable in every case.

The orthodontic system of the invention is adapted for use with a standard anatomic dental articulator device to facilitate prescribing an optimal orthodontic appliance for an individual patient, and comprises a first U-shaped element defining a substantially parallel top and bottom surface, and adapted to be positioned between a model of the upper and lower teeth in the dental articulator device so as to define the functional occlusional plane of a patient's teeth. The system also comprises a second U-shaped element defining a track around the inside surface thereof and which is removably positioned within the peripheral channel within the first U-shaped element An adjustable clamp adjustably secures the first and second U-shaped elements to the dental articulator device A tooth position calibration gauge adapts to be slidably received within the track of the second U-shaped element after the assembly of the first and second elements has been positioned in the functional occlusional plane of the model teeth and the first U-shaped element removed. Tooth pegs are adapted to be removably secured to a predetermined and anatomically correct location on the outside surface of selected teeth of the models of the patient's teeth in the dental articulator, so that re-positioning each of the selected teeth to each ideal tooth position in the functional occlusional plane is accomplished by movably positioning each of the pegs into the track of the second U-shaped element.

It is the primary object of this invention to provide an orthodontic apparatus and method for determining an optimal orthodontic appliance prescription for an individual patient through accurate, valid and reproducible calibration of tooth positions.

It is another object of the invention to provide an orthodontic apparatus and method for determining an orthodontic patient's pre-treatment and ideal post-treatment tooth positions prior to the prescription of an orthodontic appliance so that a specific and completely individualized dental occlusion and orthodontic appliance may be prescribed for an individual patient Some of the objects of the invention having been stated, other objects will become evident as the description proceeds when taken in connection with the accompanying drawings.

BRIEF DESCRIPTION OF THE DRAWINGS

FIG. 4 is a perspective view of the diagnostic occlusal track of the orthodontic system of the invention;

FIG. 5 is an end view of the diagnostic occlusal track of the orthodontic system of the invention;

BEST MODE FOR CARRYING OUT THE INVENTION

Figure 7:
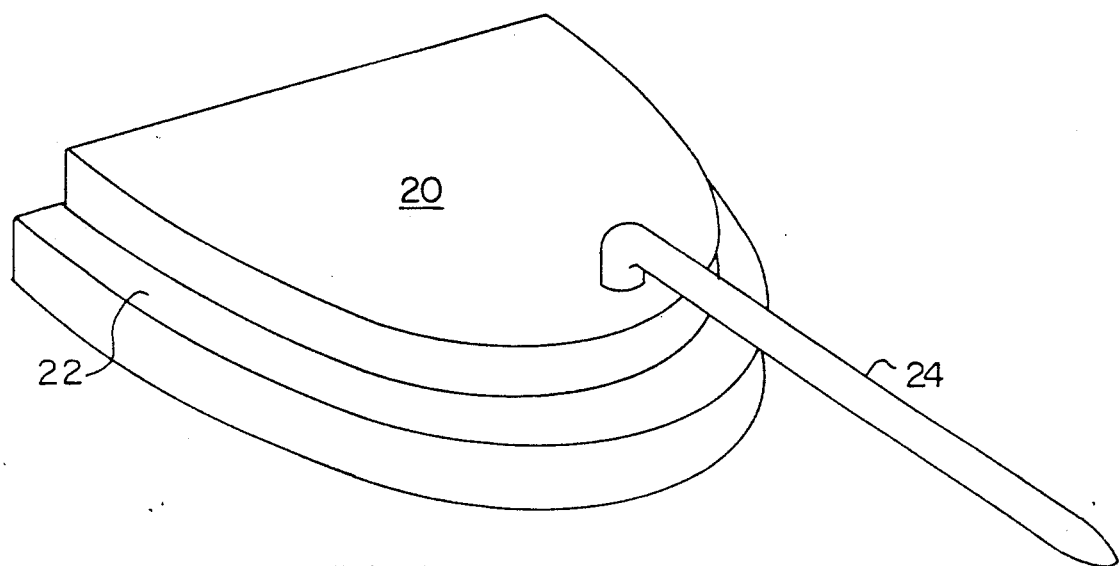
FIG. 7 is a perspective view of the diagnostic occlusal plane of the orthodontic system of the invention.
Figure 8:
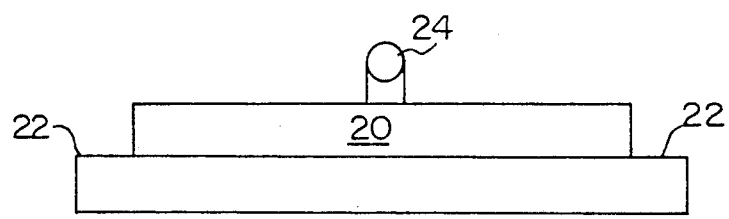
FIG. 8 is a vertical cross-sectional view of the diagnostic occlusal plane of the orthodontic system of the invention.
Figure 9:
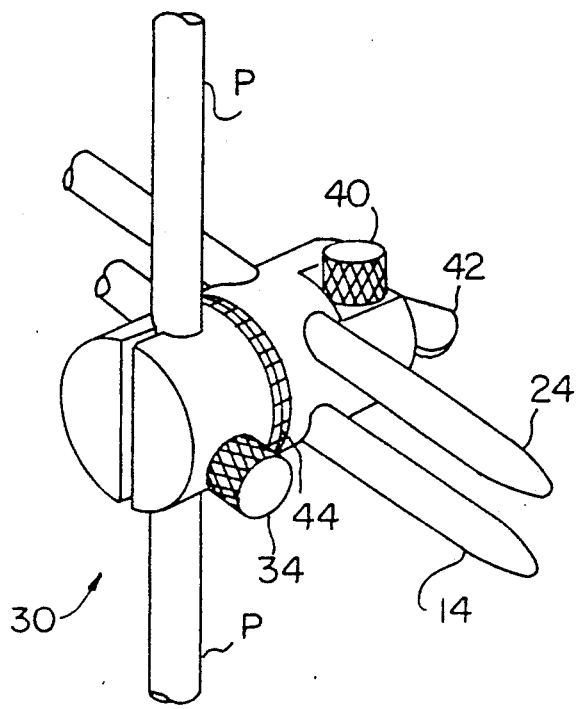
FIG. 9 is a perspective view of the clamp of the orthodontic system of the invention.
Figure 12:
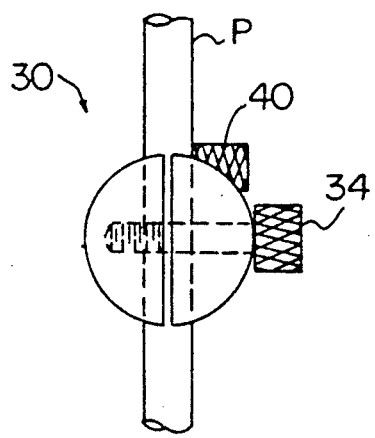
FIG. 12 is an end view of the clamp of the orthodontic system of the invention.
Figure 10:
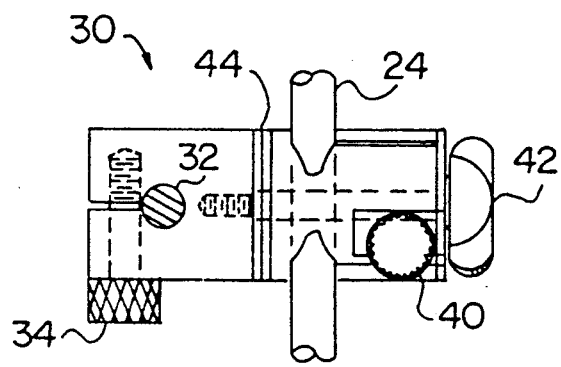
FIG. 10 is a top plan view of the clamp of the orthodontic system of the invention.
Figure 11:
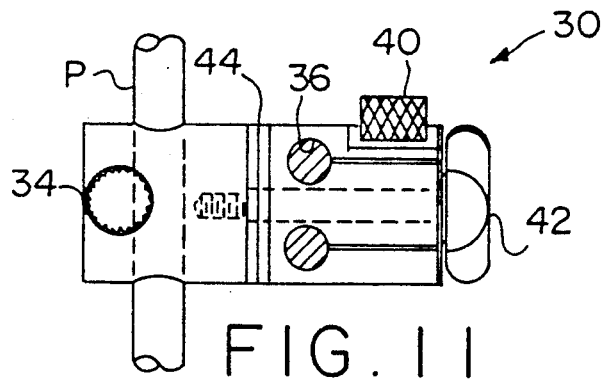
FIG. 11 is a front view of the clamp of the orthodontic system of the invention.
Figure 13:
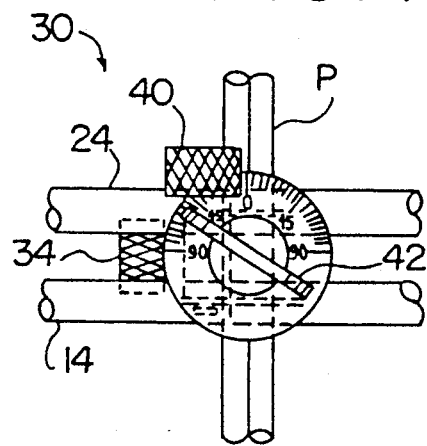
FIG. 13 is a view of the other end of the clamp of the orthodontic system of the invention.
Figure 20:
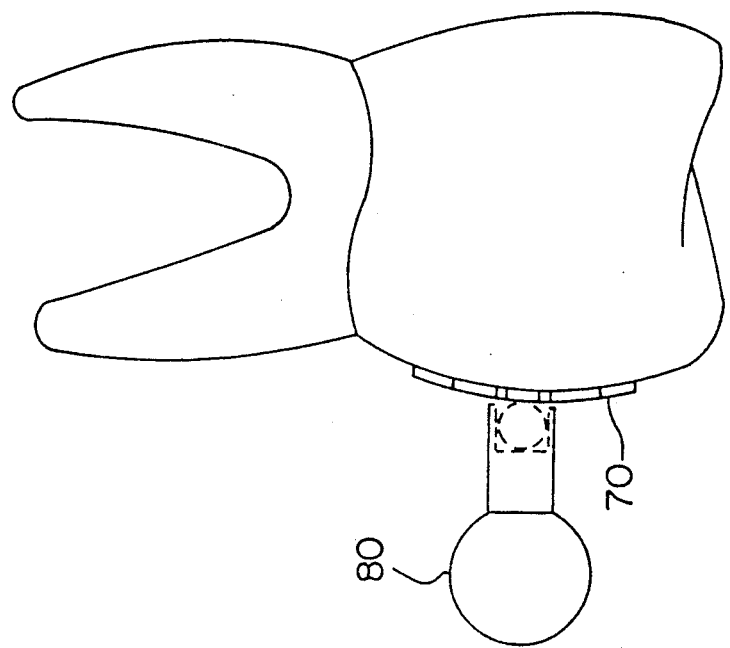
FIG. 20 is a view of a tooth peg and tooth stud assembly as affixed to a model tooth.
Figure 19:
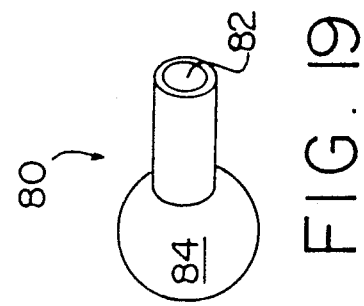
FIG. 19 is a perspective view of the tooth peg of the orthodontic system of the invention.

Referring now more specifically to the drawings, the orthodontic system of the invention for determining optimal orthodontic appliance prescription can be seen to include six novel elements The orthodontic system elements comprise a diagnostic occlusal plane (see FIGS. 7 and 8), a diagnostic occlusal track (see FIGS. 4, 5 and 6), a clamp for securing the diagnostic occlusal plane and diagnostic occlusal track to the vertical pin member of a dental articulator (see FIGS. 9-13), a calibration device for measuring the three dimensional position of each tooth (see FIGS. 14, 15, 16 and 16A), a tooth stud for each of 32 teeth (see FIG. 18), and a tooth peg for attaching over each respective tooth stud (see FIGS. 19 and 20). The six elements will now be discussed in specific detail both as to their construction and their use in the orthodontic system of the invention for determining optimal orthodontic appliance prescription.

Figure 6:
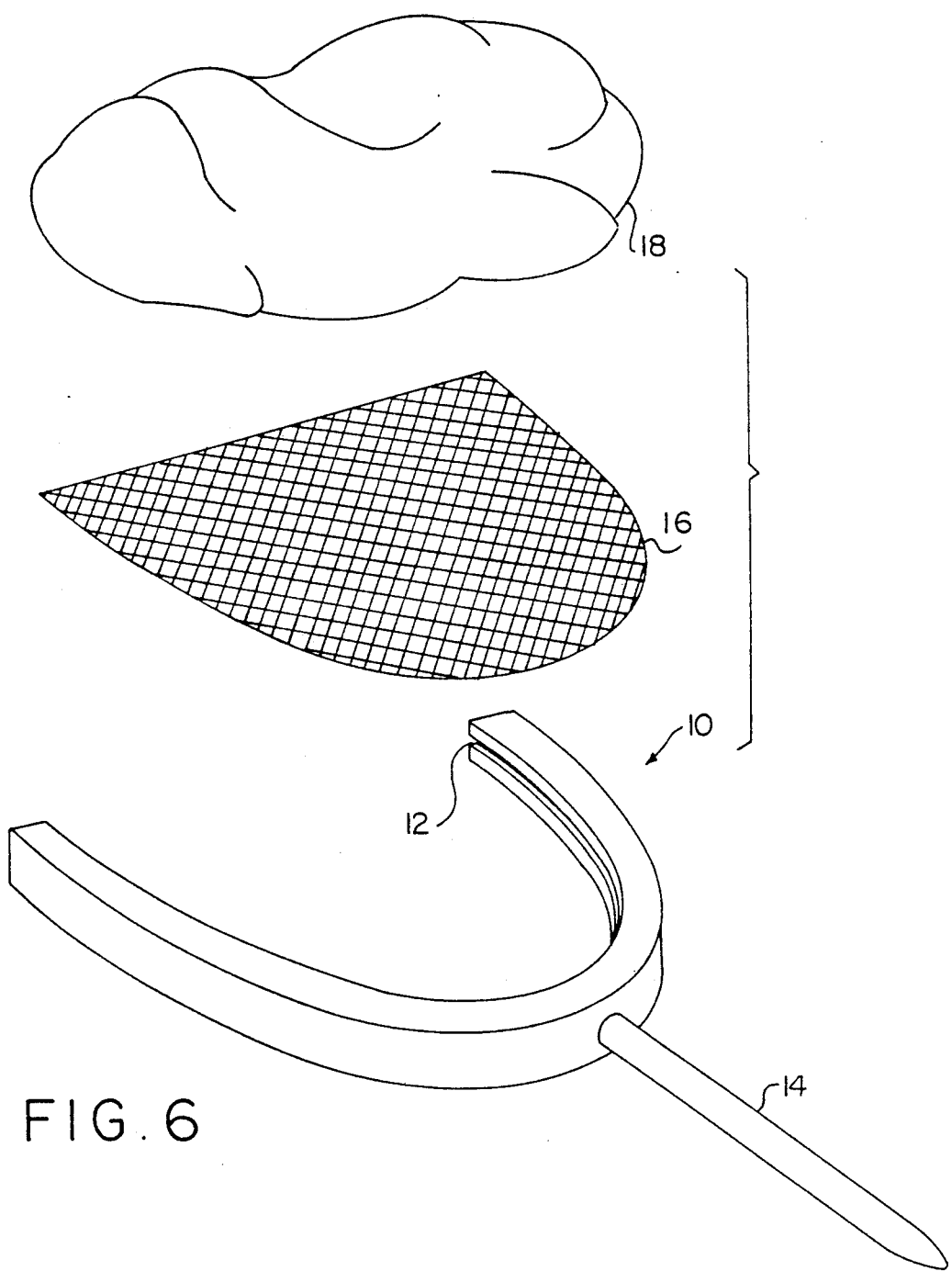
FIG. 6 is an exploded view of the diagnostic occlusal track with a disposable gauze insert and dental wax for determining the bite of the teeth and to facilitate orientation of the teeth models in a dental articulator.

First of all, with reference again to FIGS. 4, 5 and 6, diagnostic occlusal track 10 is shown which is a U-shaped element defining a slot or track 12 in the inside surface thereof and including a support arm 14 extending therefrom. As shown in FIG. 6, diagnostic occlusal track 10 is first used with a disposable cotton gauze insert 16 in the fork thereof with a suitable dental impression material such as soft dental paraffin bite wax 18 thereon and a conventional face bow transfer device (not shown) in order to obtain a valid, reproducible impression of the dental bite (occlusion) directly from the patient. With cotton gauze insert 16 and dental paraffin wax 18 positioned in the fork of diagnostic occlusal track 10, a registration is made of the biting surface of the upper and lower teeth of the patient when the patient occludes or bites together the upper and lower teeth into cotton gauze insert 16 and dental paraffin wax 18 positioned therebetween. The diagnostic occlusal track 10 with disposable insert 16 and dental paraffin impression wax 18 is then transferred and secured to a conventional dental articulator in order to orient dental hard-stone (plaster) replicas of the patient's upper and lower teeth, in a fashion of direct mimicry to the head and neck of the patient. In other words, plaster replicas of the upper and lower teeth of the patient (not shown) are positioned with the use of the tooth bite registration using a dental bite material with thixotrophic properties such as dental paraffin wax 18, carried by disposable insert 16 in diagnostic occlusal track 10.

Figure 1:
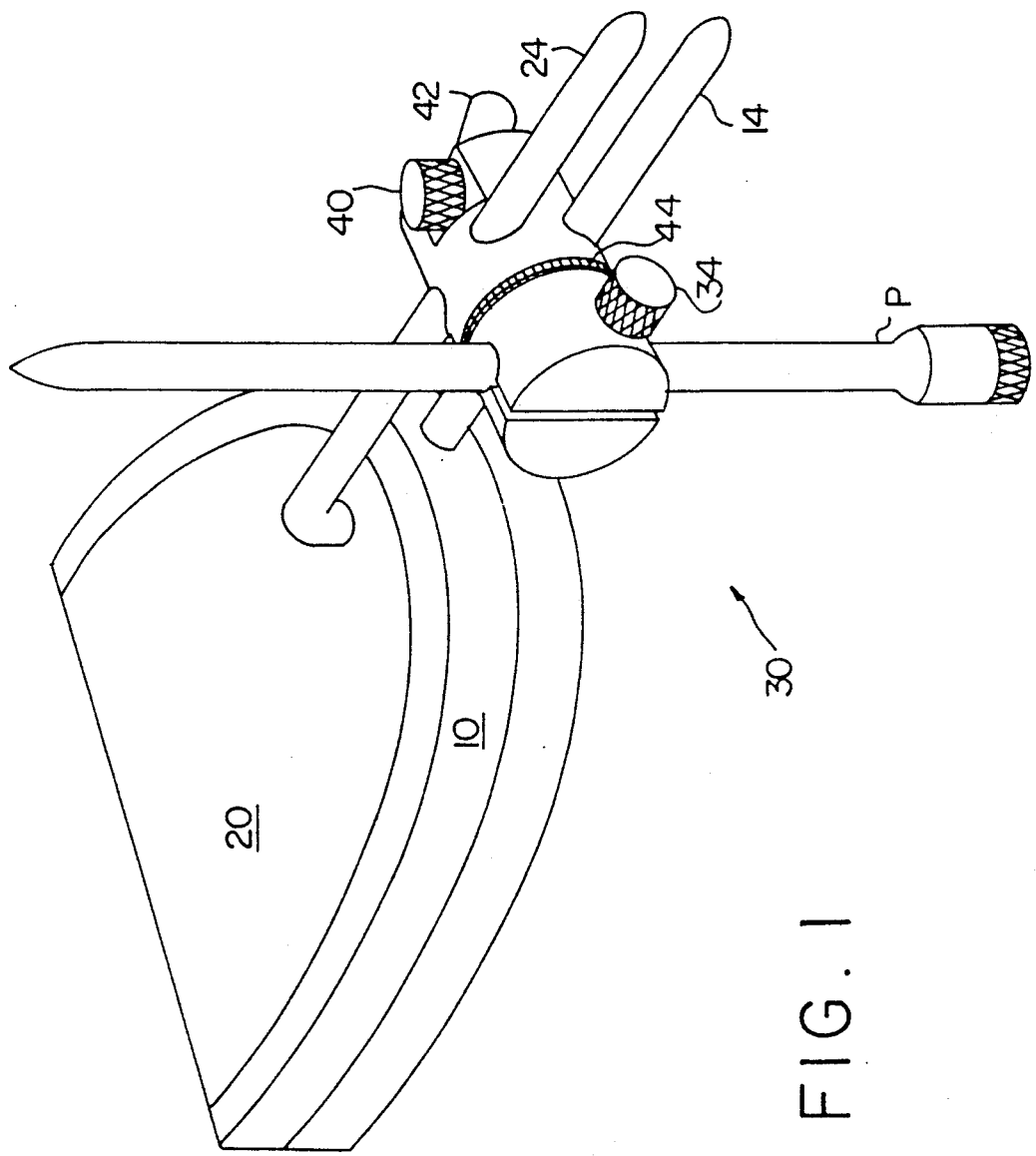
FIG. 1 is a perspective view of the diagnostic occlusal plane and diagnostic occlusal track of the orthodontic system of the invention secured to the vertical pin P of a conventional dental articulator device.
Figure 2:
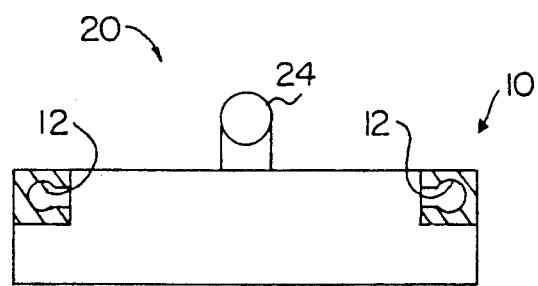
FIG. 2 is a vertical cross-sectional view taken through the diagnostic occlusal plane and diagnostic occlusal track assembly shown in FIG. 1.
Figure 3:
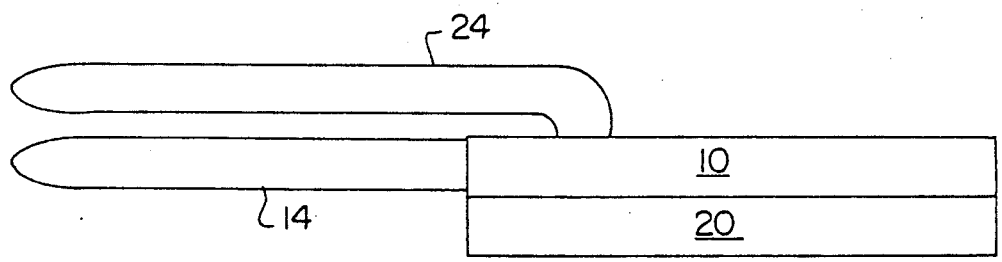
FIG. 3 is a side elevation view of the diagnostic occlusal plane and diagnostic occlusal track assembly shown in FIG. 1.

With reference to FIGS. 1-3, the disposable insert 16 and dental paraffin wax 18 are removed from dental occlusal track 10 before it is assembled with occlusal plane 20. Diagnostic occlusal track 10 is assembled together with diagnostic occlusal plane 20 (FIGS. 7 and 8) by placing diagnostic occlusal track 10 into channel 22 defined around the U-shaped perimeter of diagnostic occlusal plane 20. Diagnostic occlusal plane 20 also includes a support arm 24. Dental occlusal plane 20 with dental occlusal track 10 positioned thereon are then secured onto pin P of the dental articulator by clamp 30 (see FIG. 1 and FIGS. 9-13). Clamp 30 engages support arm 14 of occlusal track 10 and support arm 24 of occlusal plane 20 so as to adjustably secure the assembly together and to allow for adjustable positioning of the assembly of occlusal plane 20 and occlusal track 10 to establish the functional occlusal plane of the patient's model teeth in the dental articulator. The functional occlusal plane of the model teeth of the patient is determined by positioning the diagnostic occlusal assembly consisting of diagnostic occlusal plane 20 and diagnostic occlusal track 10 so that the biting surface of the upper teeth positioned in the dental articulator will rest on the upper surface of occlusal plane 20 and the biting surface of the lower teeth will touch the under surface of occlusal plane 20. Clamp 30 allows for three-dimensional movement of the occlusal assembly by permitting up and down, in and out and both lateral and vertical pivotal movement of the occlusal assembly. When the clinician is satisfied with the position of the established and calibrated functional occlusal plane in an individual patient, the diagnostic occlusal plane 20 is removed from the occlusal assembly so as to leave only the diagnostic occlusal track 10 in place at the correctly established functional occlusal plane of the upper and lower model teeth of the patient within the dental articulator.

Although the diagnostic occlusal plane assembly and track are drawn in perspective and cross-section as flat (see FIGS. 1-8), the invention further embodies the concept that the functional occlusal plane may curve in three planes of space (concavo-convex) and as such provision for such phenomenon can be made in the embodiment of the design of the invention.

In order to more fully describe clamp 30, it can been seen with particular reference to FIGS. 9-13 that clamp 30 includes a first aperture 32 therethrough for receiving vertical dental articulator pin P. Adjustment screw 34 allows for vertical adjustment and lateral pivotal adjustment of clamp 30 on articulator pin P. Clamp 30 further defines aperture 36 for receiving support arm 24 of diagnostic occlusal plane 20 and aperture 38 for receiving support arm 14 of diagnostic occlusal track 10. Adjustment nut 40 allows for "in" and "out" independent adjustment of occlusal plane 20 and occlusal track 10. Adjustment wing nut 42 allows for pivoting the section of clamp 30 carrying occlusal track 10 and occlusal plane 20 relative to the section of clamp 30 secured to articulator pin P by means of rotation washer 44. Thus, clamp 30 may be vertically adjusted on articulator pin P or pivoted thereabout with adjustment screw 34, diagnostic occlusal plane 20 and diagnostic occlusal track 10 may be adjusted "in" and "out" with adjustment screw 40, and occlusal plane 20 and occlusal track 10 may be pivoted vertically with adjustment wing nut 42. It should be appreciated that although clamp 30 has been described in significant detail with respect to the three-dimensional adjustment capabilities thereof, the orthodontic system of the present invention contemplates other embodiments of clamp 30 which would provide for three-dimensional adjustment of occlusal plane 20 and occlusal track 10.

Figure 14:
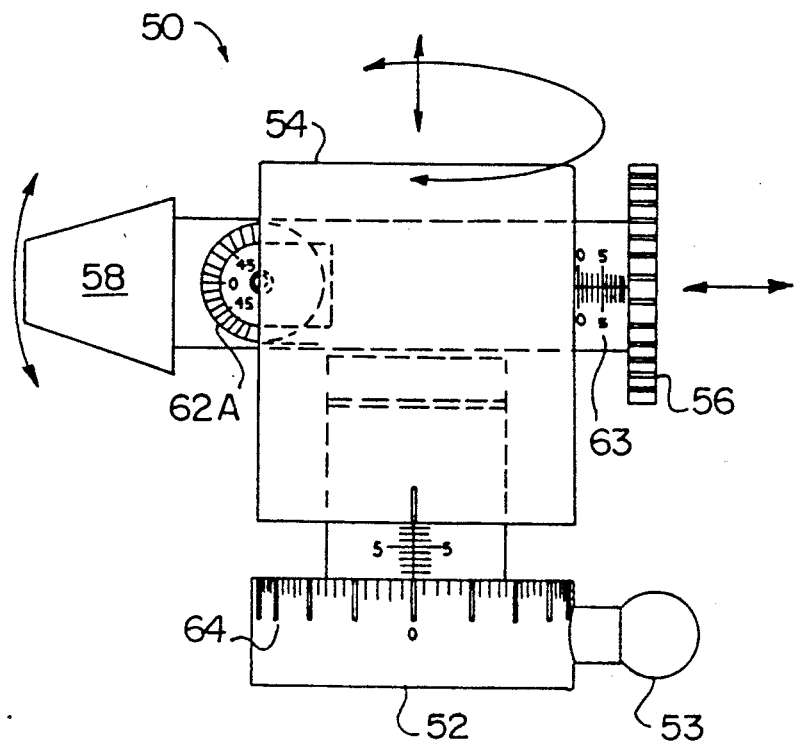
FIG. 14 is a side elevation view of the calibration gauge of the orthodontic system of the invention.
Figure 15:
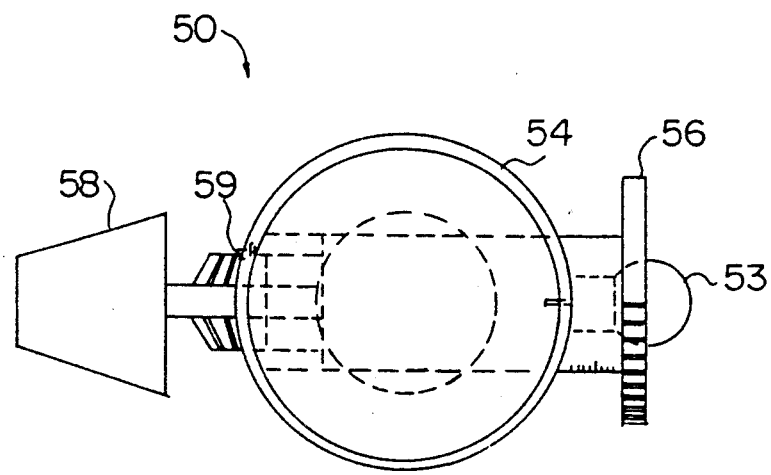
FIG. 15 is a top plan view of the calibration gauge of the orthodontic system of the invention.
Figure 16:
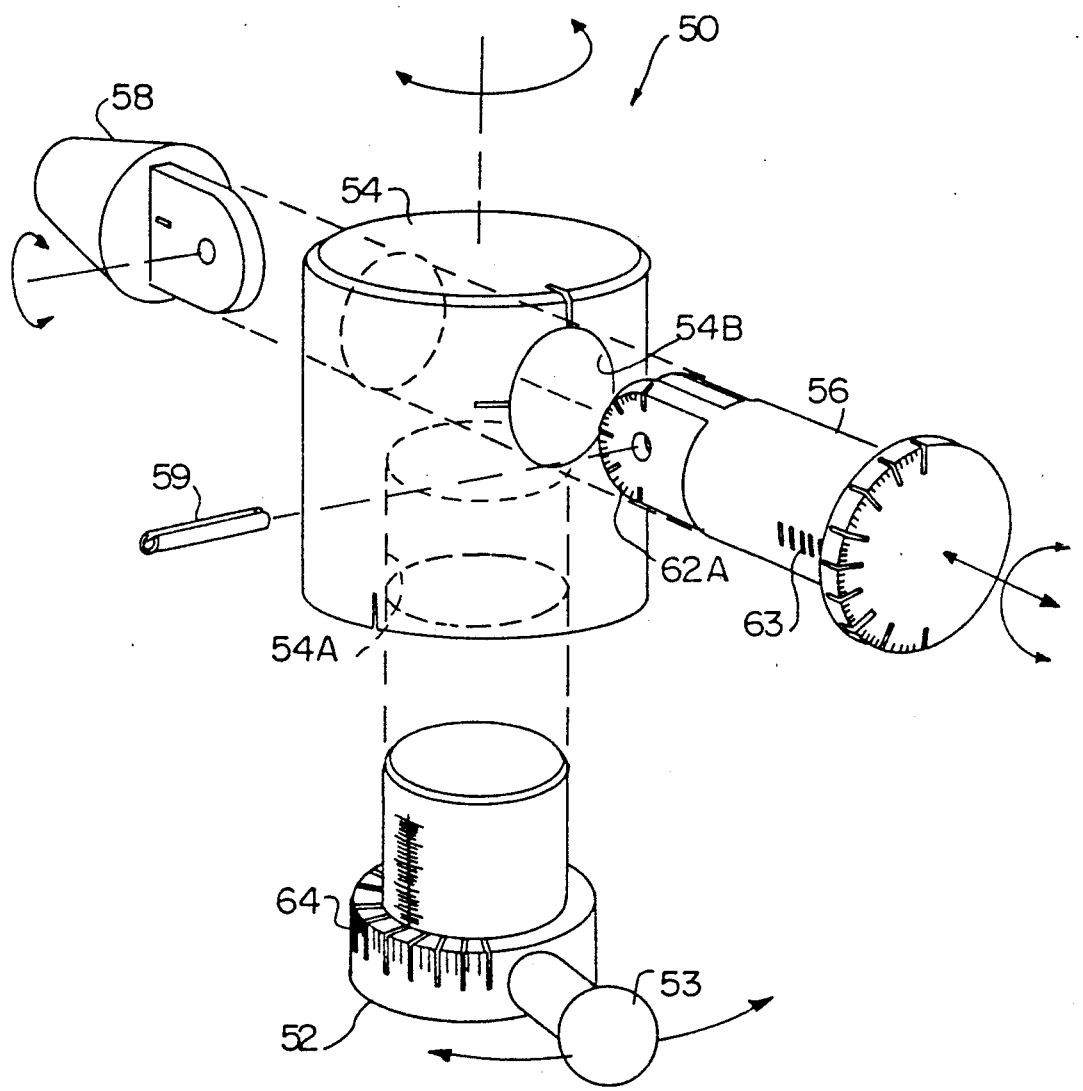
FIG. 16 is a exploded perspective view of the elements of the calibration gauge of the orthodontic system of the invention.
Figure 16A:
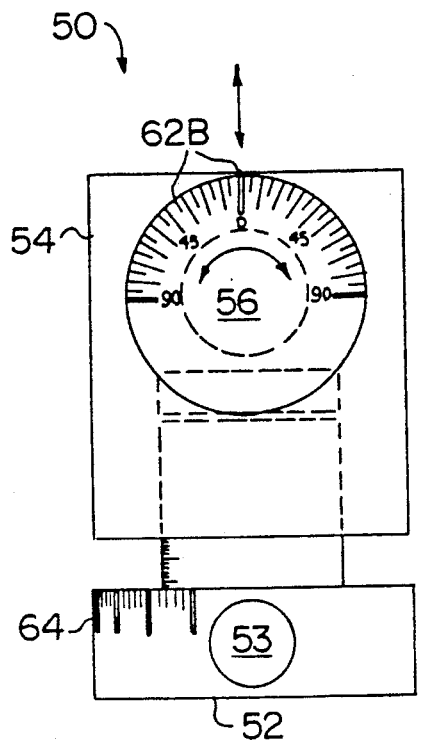
FIG. 16A is an end view of the calibration gauge of the orthodontic system of the invention.
Figure 17:
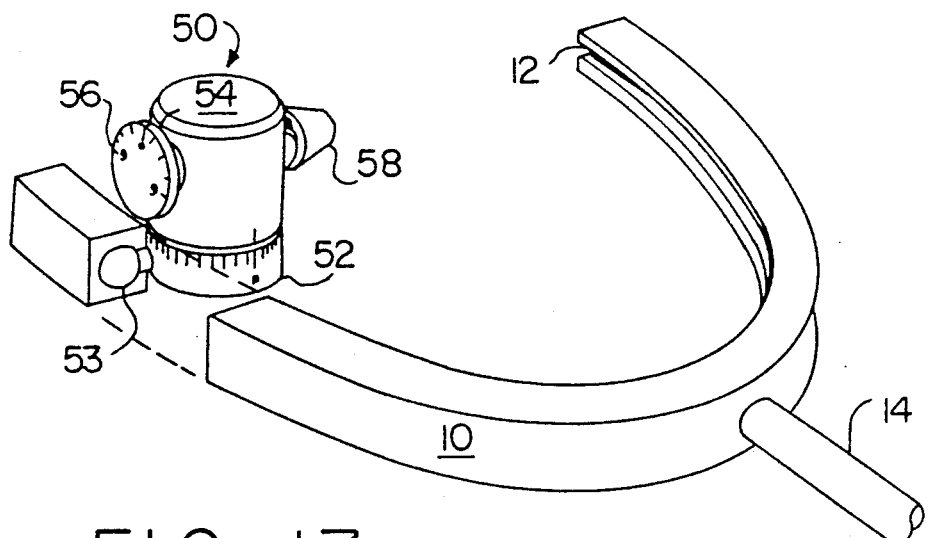
FIG. 17 is a perspective view of the calibration gauge positioned in the diagnostic occlusal track of the orthodontic system of the invention.

The next element of the system to be described is calibration gauge 50 which is shown in detail in FIGS. 14-16. It is adapted to be positioned in the track 12 of occlusal track 10 in either upright (see FIG. 17) or inverted position to measure the three-dimensional position of each tooth in the upper and lower jaw tooth models, respectively, in the dental articulator (not shown). Calibration device 50 allows for the measurement of each individual tooth's (1) tip, (2) torque, (3) in/out and (4) rotation, to aid the clinician in determining the proper tooth braces appliance prescription to be employed to correct tooth malalignment from the functional occlusion plane for a particular patient and, additionally, to aid the design of a custom appliance (where necessary) in the therapeutic correction of the patient's malaligned teeth.

Calibration gauge 50 comprises a base 52 with a sphere 53 extending therefrom which can be slidably and accurately positioned in track 12 of occlusal track 10. Sleeve 54 defines first aperture 54A in the bottom thereof and second aperture 54B laterally through the top thereof. Thus, sleeve 54 slidably receives and is rotatably positioned on base 52 and horizontal aperture 54B of sleeve 54 carries in/out slide 56. Sleeve 54 may move both vertically and rotatably when mounted on base 52. In/out slide 56 has vertically pivotable tip arm 58 mounted thereon so as to pivot up and down about hinge 59 (see FIG. 15), and both tip arm 58 and in/out slide 56 may rotate 360° within sleeve 54. Thus, the three-dimensional position measurements of each plaster model tooth in the dental articulator may be taken by sliding calibration gauge 50 in its upright position along track 12 of diagnostic track 10 for the upper model teeth and inverting it for measuring (calibrating) positions for the lower model teeth. For each tooth calibration, gauge 50 is positioned adjacent the tooth to be measured and tip arm 58 brought into contact with an anatomic central position of each tooth in order to determine its tip position which is indicated by the measurement scale 62A (which indicates the degree of tip arm 58 relative to in/out member 56) and measurement scale 62B (which indicates the degree of tip arm 58 relative to sleeve 54). Measurement scale 62A defined between tip arm 58 and in/out slide 56 indicates the tip of the tooth on the basis of up and down movement of tip arm 58 relative to in/out slide 56, and measurement scale 62B defined between the outside end of in/out slide 56 and sleeve 54 (see FIG. 16A) indicates the tip of the tooth on the basis of rotational movement of in/out slide 56 relative to sleeve 54. Measurement scale 63 defined between sleeve 54 and in/out slide 56 provides an in/out measurement of the position of the tooth, and measurement scale 64 defined between sleeve 54 and base 52 provides measurement data relating to the rotational position of the tooth. In this fashion, the three-dimensional position of each tooth of the individual patient can be determined from the model teeth in the dental articulator by use of calibration gauge 50.

Figure 18:
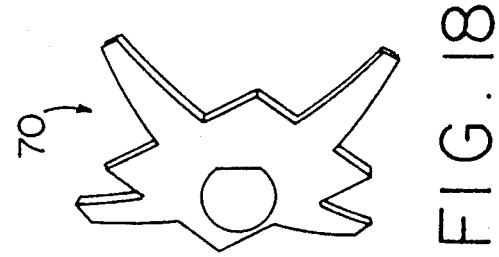
FIG. 18 is a perspective view of the tooth stud of the orthodontic system of the invention.

Once the pre-orthodontic treatment position of the teeth is known, the orthodontic system for determining optimal orthodontic appliance prescription may be used to determine the ideal post-treatment tooth location where the individual teeth of the model are individually and collectively set to the absolute registration of the functional occlusal plane. To do so, calibration gauge 50 and occlusal track 10 are removed from between the upper and lower model teeth. Next, a tooth stud or tooth base member 70 (see FIG. 18) is attached to a predetermined location on each of the model teeth. The present invention contemplates that individual tooth studs or tooth base members 70, as shown in FIG. 18, are fabricated so as to precisely fit to a predetermined, central surface location on each upper and lower tooth. Since there are normally 32 teeth in the human patient, the system of the invention provides 32 individual tooth base members 70 so that each tooth has a precisely fabricated base member for attachment to that particular tooth. The tooth studs or tooth base members 70 are attached to the outside surface of each tooth with a readily dissolvable adhesive. In this fashion, although rigidity is obtained for the tooth base members 70, these can be easily removed without damage to the plaster models in the dental articulator after repositioning of the teeth to the ideal post-treatment location. A set of 32 tooth pegs 80 (see FIG. 19) are also provided by the system of the invention which are interchangeably placeable over the spherical member of each tooth base member 70. Tooth pegs 80 each define an open sleeve 82 at one end to receive a base member 70 and a designed spherical member 84 at the other end thereof which is machined and sized so as to fit snugly and slide precisely into and along track 12 of occlusal track 10.

Once base members 70 and corresponding tooth pegs 80 have been attached to individual teeth requiring repositioning due to incorrect tooth malalignment from the functional occlusal plane (malocclusion), the teeth are moved to their desired position in the previously established functional occlusal plane by returning occlusal track 10 to its position in the functional occlusal plane and sliding the spherical ends 84 of pegs 80 into track 12 of occlusal track 10. This can be accomplished since the model teeth in the dental articulator are affixed to their plaster bases on the dental articulator with dental modeling wax. Thus, the tooth base wax may be softened with moderate heat during the positioning of the teeth to the ideal post-treatment position and then the wax allowed to cool to room temperature and revert to its solid state so as to secure the teeth in their newly, correctly repositioned location.

Although many construction materials are possible for the components of the system, applicant presently contemplates that occlusal plane 20, occlusal track 10 and calibration device 50 will be fabricated of a light alloy (aluminum). Clamp 30 and base members 70 and tooth pegs 80 may be fabricated of either alloy or a polymer material.

Now that all of the elements of the system of the present invention have been described in detail, it can be appreciated that the system for determining optimal orthodontic appliance prescription provides for enhanced orthodontic treatment by allowing for individualized orthodontic appliance or tooth braces prescription on the basis of calibrated individual pre-treatment tooth position and calibrated ideal individual post-treatment tooth position before the application of tooth braces.

METHOD OF OPERATION

In operation, the system of the invention is used by the clinician by first orienting plaster replicas of the patient's upper and lower teeth on a dental articulator with use of the bite registration obtained in dental impression wax 18 carried by occlusal track 10 which has been secured appropriately to the dental model articulator. Once the replicas of the upper and lower teeth in both jaws of the patient are properly oriented, removable gauze insert 16 and dental impression wax 18 are removed from the fork of occlusal track 10.

Occlusal plane 20 is now assembled with occlusal track 10 and secured to upstanding pin P of the dental articulator with clamp 30 in order that the functional occlusal plane of the patient's teeth can be properly established. The functional occlusal plane is determined by positioning the aforementioned assembly of occlusal plane 20 and occlusal track 10 such that the upper jaw teeth contact the top surface of occlusal plane 20 and the lower jaw teeth contact the bottom surface of occlusal plane 20. The position of the functional occlusal plane is then recorded on pin P (FIG. 1) of the dental articulator so that the assembly of occlusal track 10 and occlusal plane 20 may be removed and replaced without having to again determine the functional occlusal plane from the patient.

Next, tooth calibration device 50 is placed into track 12 of occlusal track 10 and three-dimensional measurements are taken of the position of each tooth in the plaster replicas of the patient's teeth relative to the previously determined functional occlusal plane and then all measurements of tooth positions are recorded. The upper teeth are measured by positioning calibration device 50 in track 12 in the upright position, and the lower jaw teeth are measured by positioning calibration device 50 in a similar but inverted fashion in track 12 of occlusal track 10. Once the pre-treatment tooth positions (tip location, in-out, torque and rotation) have been measured by calibration device 50, the assembly of occlusal track 10 and occlusal plane 20 is removed from the dental articulator.

Now that the pre-orthodontic treatment tooth positions have been measured, the system is next used to determine the ideal post-treatment tooth location. To do so, tooth base members 70 are affixed with an appropriate adhesive to each tooth which requires repositioning in the upper and lower jaws. Tooth pegs 80 are attached to the base members by sliding the hollow sleeve end 82 of peg 80 over the spherical member of base member 70. The teeth requiring repositioning in order to be in the previously determined functional occlusal plane are repositioned by first softening their supportive base wax with moderate heat and then sliding spherical end 84 of tooth peg 80 affixed thereto into the slot or track 12 of occlusal track 10 which has now again been positioned in the functional occlusal plane and secured to dental articulator pin P. The supportive base wax of the repositioned teeth is allowed to cool and solidify so as to secure the repositioned teeth in their new location in the functional occlusal plane. Once all teeth requiring repositioning have been in this fashion repositioned into the functional occlusal plane, calibration device 50 may again be placed in track 12 of occlusal track 10 and used to measure and check the repositioned teeth to assure that they are properly positioned in the functional occlusal plane. This step can be performed only after base members 70 and tooth pegs 80 have been removed from the teeth.

In summary, applicant provides a novel orthodontic system for determining optimal orthodontic appliance prescription for an individual patient by providing for pre-orthodontic treatment tooth position measurement and ideal post-orthodontic treatment tooth position measurement of dental models to facilitate prescribing the optimal tooth brace prescription for each patient.

It will be understood that various details of the invention may be changed without departing from the scope of the invention. Furthermore, the foregoing description is for the purpose of illustration only, and not for the purpose of limitation—the invention being defined by the claims.

What is claimed is:

1. A system for use with a dental articulator device to determine and calibrate both preorthodontic treatment and ideal post-treatment tooth positions in order to facilitate prescribing an optimal orthodontic appliance for an individual orthodontic patient, said system comprising:
    a first U-shaped element defining a substantially parallel top and bottom surface and sized to fit between a model of the upper and lower teeth in said dental articulator device so as to define the functional occlusal plane of the patient's teeth;
    a second U-shaped element defining an elongate track around at least a majority of the inside surface thereof and adapted to be removably positioned on said first U-shaped element;
    clamp means for adjustably securing said first and second U-shaped elements to said dental articulator device and providing for three-dimensional adjustment thereof relative to said dental articulator device;
    measurement means for determining the position of selected teeth in said model of the patient's upper and lower teeth in said dental articulator device wherein said measurement means comprises a calibration device having a laterally extending track engaging element at one end adapted to be slidably received within the track of said second U-shaped element and a tooth position calibrator extending laterally from the other end of said calibration device in opposing direction to said track engagement element; and
    peg means for re-positioning each of selected teeth into its ideal position in the functional occlusional plane of the patient's teeth, said peg means comprising a plurality of base elements wherein each base element is adapted to be adhesively mounted to a tooth in the model of the patient's upper and lower teeth, and a plurality of elongate pegs adapted to engage a corresponding plurality of said base elements at one end and to be slidably received within the track of said second U-shaped element at the other end thereof.

2. A system according to claim 1 wherein said first U-shaped element comprises a rigid block defining a channel around the perimeter of the top surface thereof for removably receiving said second U-shaped element therein.

3. A system according to claim 2 wherein said first U-shaped element comprises an arm extending outwardly therefrom for removable engagement by said clamp means.

4. A system according to claim 1 wherein said track defined by said second U-shaped element extends around substantially the entire inside surface thereof.

5. A system according to claim 4 wherein said second U-shaped element comprises an arm extending outwardly therefrom for removable engagement by said clamp means.

6. A system according to claim 1 wherein said clamp means is movably securable to said dental articulator means and provides for three-dimensional adjustment of said first and second U-shaped elements supported thereby.

7. A system according to claim 1 wherein said calibration device is adapted to measure tooth tip, torque, in-out and rotation.

8. A system according to claim 1 wherein said base elements each define an outwardly extending spherical element, and said pegs each define an aperture at one end for snugly receiving the spherical element of one of said base elements and an enlarged, sphere at the other end for slidably engaging the track of said second U-shaped element.

9. A system according to claim 1 wherein said plurality of base elements comprises 32 base elements and said plurality of elongate pegs comprises 32 sleeves.

10. A system according to claim 1 wherein each of said plurality of base elements is adapted to be mounted to a specific tooth in the model of the patient's upper and lower teeth.

11. A method for determining both pre-orthodontic treatment tooth position and ideal post-treatment tooth position to facilitate prescribing an optimal orthodontic appliance for an individual orthodontic patient, said method comprising the steps of:
    positioning a model of the upper and lower teeth into a dental articulator so as to correspond to the natural orientation of the patient's teeth;
    adjustably securing a diagnostic assembly to the dental articulator, said assembly comprising a first U-shaped element defining a substantially parallel top and bottom surface with a channel around at least a portion of the perimeter of the top surface, and a second U-shaped element removably residing within said channel of said first U-shaped element and defining a track around at least a portion of its inside surface;
    determining the functional occlusal plane of the patient's teeth by positioning the diagnostic assembly so that the model upper teeth contact the top surface of said first U-shaped element and the model lower teeth contact the bottom surface thereof;
    removing said first U-shaped element so that said second U-shaped element remains in place in the functional occlusal plane of the model of the patient's upper and lower teeth positioned on the dental articulator;
    sliding a calibration device within the track of said second U-shaped element so as to measure the three-dimensional pre-treatment position of selected model teeth relative to the functional occlusal plane;
    securing an elongate peg element to a predetermined position on the outside surface of selected model teeth; and
    repositioning the selected model teeth into the functional occlusal plane by sliding the free end of each elongate peg elements into the track of said second U-shaped element and thereby determining the ideal post-treatment position of the model teeth.

12. A method according to claim 11 wherein said positioning includes orienting the model teeth in the dental articulator by providing a removable gauze insert with dental wax thereon in said first U-shaped insert, allowing the patient to bite thereon, and securing the first U-shaped element with the registration of the patient's teeth biting surface in the dental articulator to provide for proper registration of the model teeth in the articulator.

13. A method according to claim 11 including measuring the three-dimensional post-treatment position of each model tooth relative to the functional occlusal plane by first removing said elongate peg elements from the model teeth and then again sliding the calibration device within the track of said second U-shaped element so as to measure the three-dimensional position of each model tooth relative to the functional occlusal plane.

* * * * *